US008974842B2

(12) United States Patent
Pecher et al.

(10) Patent No.: US 8,974,842 B2
(45) Date of Patent: Mar. 10, 2015

(54) METHOD FOR PREPARING A LIPOPHILIC VINE EXTRACT

(75) Inventors: Virginie Pecher, La Chapelle Saint Mesmin (FR); Patrice Andre, Neuville aux Bois (FR)

(73) Assignee: L V M H Recherche (FR)

( * ) Notice: Subject to any disclaimer, the term of this patent is extended or adjusted under 35 U.S.C. 154(b) by 898 days.

(21) Appl. No.: 12/460,742

(22) Filed: Jul. 23, 2009

(65) Prior Publication Data

US 2010/0034764 A1 Feb. 11, 2010

(30) Foreign Application Priority Data

Jul. 25, 2008 (FR) ...................................... 08 55117

(51) Int. Cl.
*A61K 36/87* (2006.01)
*A61K 36/00* (2006.01)
*A61K 8/34* (2006.01)
*A61K 8/97* (2006.01)
*A61Q 1/10* (2006.01)
*B01D 11/02* (2006.01)

(52) U.S. Cl.
CPC . *A61K 8/347* (2013.01); *A61K 8/97* (2013.01); *A61Q 1/10* (2013.01); *B01D 11/0203* (2013.01)
USPC ............................. 424/766; 424/725; 424/779

(58) Field of Classification Search
None
See application file for complete search history.

(56) References Cited

U.S. PATENT DOCUMENTS

2003/0114708 A1* 6/2003 Jerz ................................ 562/498
2007/0243148 A1 10/2007 Andre et al.
2009/0035839 A1* 2/2009 Katz et al. ..................... 435/243

FOREIGN PATENT DOCUMENTS

| CN | 1628774 A | * | 6/2005 |
| EP | 0464297 A1 | | 1/1992 |
| EP | 1820492 A1 | | 8/2007 |
| JP | 06211673 A | * | 8/1994 |
| JP | 2001292731 A | | 10/2001 |
| KR | 20060093145 A | | 8/2006 |
| KR | 20070066452 A | | 6/2007 |
| WO | 0103713 A1 | | 1/2001 |
| WO | 02092042 A2 | | 11/2002 |

OTHER PUBLICATIONS

Pomace from Wikipedia, the free encyclopedia, accessed on Nov. 4, 2010, pp. 1-4.*
Mantell et al, Supercritical fluid extraction of anthocyanins form grape pomace, Solvent extraction for the 21st century, proceedings of ISEC'99, 1999, vol. 2, 1615-1618.*
Tripathi, Fungicidal activity of the root extracts of *Vitis vinifera*, Asian Journal of Chemisty, 13 (1): 353-354, 2001.*
Lee et al, Extraction of grape seed oil by supercritical CO2 and ethanol modifier, Food Sci Biotehnol. 9 (3): 174-178, 2000.*
Ruberto et al, Volatile components of grape pomaces from different cultivars of Sicilian *Vitis vinifera* L., Bioresource technology, (Jan. 2008) vol. 99, No. 2, pp. 260-268.*
Definition of shoots from Dictionary.com, accessed on Feb. 28, 2011, pp. 1-4.*
Definition of Stalk from Dictionary.com, accessed on Feb. 28, 2011, pp. 1.*
Yu et al, Supercritical CO2 extraction of resveratrol and its glycoside piceid from Chinese traditional medicinal herb *Polygonum cuspidatum*, Journal of the science of food and agriculture, Feb. 2005 vol. 85, No. 3 p. 489-492.*
Mirsra et al, Chemical constituents of *Hyptis suaveolens*. Part I. Spectral and biological studies on a triterpene acid, Journal of Natural Products, 44 (6): 735-738, 1981.*
Stock from Merriam-Webster, accessed on Jul. 6, 2011, pp. 1-5.*
French Search Report, FR0855117, 2009.

* cited by examiner

*Primary Examiner* — Qiuwen Mi
(74) *Attorney, Agent, or Firm* — Lerner, David, Littenberg, Krumholz & Mentlik, LLP

(57) ABSTRACT

The present invention relates to a method for preparing a lipophilic extract from lignified portions of vine, such as shoots, stock and roots, characterized in that said method comprises a step for extraction from said lignified portions with an apolar solvent; to an extract obtained by such a method; to the use of such an extract as an excipient in a cosmetic composition; and to a cosmetic composition comprising such an extract.

12 Claims, No Drawings

METHOD FOR PREPARING A LIPOPHILIC VINE EXTRACT

The present invention relates to a method for preparing a lipophilic vine (*Vitis vinifera*) extract, to the lipophilic extract obtained by this method as well as to the use of said extract as an excipient in cosmetic compositions.

More specifically, said lipophilic vine extract is an extract from the lignified portions of the plant, i.e., essentially the stock, the roots and the shoots.

The extracts of vine shoots and roots have many interesting cosmetic properties. The extracts of vine shoots thus comprise significant concentrations of resveratrol and ϵ-viniferin (dimer of resveratrol). Resveratrol notably has antioxidant properties and also fungicidal and bactericidal properties.

A method for extracting resveratrol and/or ϵ-viniferin from dry vine shoots is known from document FR 2795965. Maceration of shoots, peduncles and vine leaves in a solvent having a carbonyl radical such as an ester or a ketone, or in an alcohol, leads to an extract containing high contents of these substances.

FR 2896990 discloses a protective and regenerative cosmetic composition comprising a combination of cosmetic active agents among which a dried vine shoot extract is obtained with polar solvents, notably a lower $C_1$-$C_6$ alcohol or a ketone, either pure or mixed with water, said composition enabling anti-aging cosmetic care and revitalization of the skin.

In spite of their interesting properties, these extracts are not very used in cosmetics because of the low extraction yields on these vine portions and also because of their unsuitable coloration with view to cosmetic use.

The inventors of the present application have shown that by extracting certain vine portions with an apolar solvent and in particular with carbon dioxide ($CO_2$) in subcritical or supercritical state, it is possible to obtain a lipophilic extract capable of forming homogenous mixtures with fats by miscibility or co-solubility. Further, this extract has a consistency such that it makes it of high interest for its use as an excipient in cosmetic compositions, in particular in those comprising at least one fatty phase.

A further advantage is to have a method for preparing the extract of the invention enabling to achieve a mass yield compatible with industrial use.

Further, this extraction method has the advantage of providing an extract directly in a colorless or slightly colored form, which avoids an additional discoloration step, for example by passing over activated charcoal particles, such a step triggering potentially the lowering of the mass yield.

The substantial absence of coloration is related to the selection of the extraction solvent and to the experimental conditions of the extraction method which avoid the stripping of a too large amount of pigments present in the plant tissues, and notably chlorophyll.

Accordingly, a first object of the invention relates to an extraction method from lignified portions of vine (*Vitis vinifera*) such as shoots, stock or roots, characterized in that said method comprises an extraction step for said lignified portions with an apolar solvent.

Apolar solvents are those which may be used as solvent in an extraction method for plant tissues, among which, as an example, mention may notably be made of alkanes, notably $C_6$ or $C_7$ alkanes such as cyclohexane, n-hexane or heptane, or also carbon dioxide ($CO_2$).

The object of the invention is more particularly an extraction method for lignified vine portions in which the extraction solvent is carbon dioxide in supercritical or subcritical state.

The supercritical state for a fluid is defined as being the state in which this fluid is found when it is subject to temperature and pressure conditions such that the applied temperature is above a critical temperature (Tc) and the applied pressure is higher than a critical pressure (Pc), these critical values being specific to each fluid.

For carbon dioxide, the critical temperature Tc is equal to 31° C. and the critical pressure Pc is equal to $7.38.10^6$ Pa.

The subcritical state is defined as the state in which a fluid is found, when the temperature to which it is subject, is less than the critical temperature Tc (Tc=31° C. for carbon dioxide), the pressure P being then able to be indifferently less or higher than the critical pressure (Pc=7.38.10 Pa for carbon dioxide).

The temperature and pressure conditions are adapted so as to place carbon dioxide in the desired state, however the pressure may represent a value ranging up to 300 times the atmospheric pressure (1 atm=$0.101.10^6$ Pa), but a pressure comprised between $8.10^6$ Pa and $30.10^6$ Pa is preferentially used for extraction with carbon dioxide in the supercritical state, and comprised between $6.5.10^6$ Pa and $10.10^6$ Pa for an extraction in the subcritical state.

Advantageously, carbon dioxide is compressed to a pressure above $7.4.10^6$ Pa, preferably higher than or equal to 18.106 Pa and more preferably higher or equal to $25.10^6$ Pa.

More advantageously, the extraction is carried out at a temperature comprised between 15° C. and 80° C.

Preferably, said extraction is an extraction with carbon dioxide in the supercritical state.

This method of extraction with sub- or super-critical carbon dioxide generally has the advantage of not requiring organic solvents, which have undesirable effects in the context of cosmetic use (e.g., toxicity and/or irritation).

However, as additional means, organic solvents may optionally be used, as a stripping agent or co-solvent in the extraction method according to the invention, in order to modify the polarity of the mixture formed with carbon dioxide, to reinforce the solvent power towards certain molecules which are not very soluble or not soluble at all in carbon dioxide in the supercritical or subcritical state and/or to facilitate the stripping of the formed mixture.

As an example, ethanol is mentioned as solvent which may be used for modifying the polarity of the mixture formed with carbon dioxide, and fatty acid esters such as for example dicaprylyl carbonate (Cetiol CC®, Cognis GmbH), cetearyl isononanoate Cetiol SN®, Cognis GmbH) or further caprylic/capric triglyceride (Mygliol 812®, Hüls AG), as solvent which may be used as stripping agent.

When one of these organic solvents is used during the extraction, its concentration is less than or equal to 5% by weight relatively to the carbon dioxide used for the extraction.

At the end of the actual extraction step, an expansion phase by lowering the pressure and optionally the temperature, causes carbon dioxide to pass from the subcritical or supercritical state to the gas state, which enable to remove completely the carbon dioxide from the obtained extract. This step also removes the organic solvent optionally used as a stripping agent or co-solvent.

An optional additional step may consist in a drying step in order to remove any trace of residual water in the extract obtained by the extraction method according to the invention. This drying step preferentially consists in an operation for freeze-drying the obtained extract.

Within the scope of the method according to the invention, any type of vine variety may be used, in particular Merlot, Cabernet Franc, Gamay, Syrah, Sémillon or Sauvignon varieties. Preferably, the varieties used, treated together or separately, are the Sémillon variety and the Sauvignon variety.

The method of the invention may be applied to the different lignified portions of the vine, such as the shoots, stocks and roots, treated together or separately.

These lignified vine portions are preferentially subjected to a milling step before the extraction step.

According to a first preferred embodiment, the method according to the invention is a method for extraction from vine shoots.

According to a preferred embodiment, dried shoots are used.

By dried shoots are meant vine shoots which have been subject to a drying step so as to advantageously have a humidity level of less than 20%, preferably less than 5% by weight. According to an alternative embodiment, drying of the shoots is either achieved via a natural route in free air in a dry place, or by drying in an oven at a moderate temperature, for example not exceeding about 40° C., until a humidity level in each case of less than 20%, preferably less than 5% by weight is obtained. For example drying may be achieved via a natural route, in free air in a dry place, according to the drying method recommended in document WO 01/03713, and comprising in particular a drying time period of at least two months, preferably at least four months.

Advantageously, extraction from the dried shoots is carried out at a temperature less than the critical temperature of carbon dioxide (31° C.), preferably carried out at a temperature ranging from 18° C. to 25° C. and more preferably of 20° C.

According to a preferred embodiment, the extraction from the dried shoots is carried out at the temperature of 20° C. and the pressure of $29.10^6$ Pa.

Still advantageously, the extraction is carried out with carbon dioxide in the absence of any co-solvent.

Finally, because of the quality of the obtained lipophilic extract (low chlorophyll content), said extraction method does not require any additional discoloration step.

According to a second preferred embodiment, the method according to the invention is a method for extraction from vine roots.

According to another preferred embodiment, dried roots are used.

By dried vine roots are meant roots having characteristics identical with those of the dried vine shoots described earlier.

Advantageously, extraction from dried vine roots is carried out at a temperature above the critical temperature of carbon dioxide (31° C.), preferably the extraction is carried out at a temperature ranging from 35° C. to 80° C. and more preferably of 60° C.

According to a preferred embodiment, the extraction from the dried roots is carried out at a temperature of 60° C. and the pressure of $29.10^6$ Pa.

Still advantageously, the extraction is carried out in the presence of at least one co-solvent, said co-solvent being preferably ethanol.

The co-solvent concentration is advantageously higher than or equal to 1% by weight relatively to the carbon dioxide used for the extraction and preferably comprised between 3% and 5% by weight.

A second object of the invention relates to a lipophilic extract from lignified vine portions, such as shoots, stocks or roots, which may be obtained by the extraction method as defined earlier.

The lipophilic extract from lignified vine portions within the scope of the invention, is any extract from vine shoots, stocks or roots harvested in a vineyard, preferably vine shoots of the Sémillon variety and/or Sauvignon variety.

The obtained lipophilic extract is found in the solid or semi-solid state at room temperature.

Finally, a third object of the invention relates to the use of a lipophilic extract from lignified vine (*Vitis vinifera*) portions, such as vine shoots, stocks or roots, as an excipient in a cosmetic composition.

Indeed, the extract obtained by the extraction method described earlier is rich in fats, which provides consistency and texture to the touch, which makes it particularly suitable for cosmetic use, notably as an excipient in cosmetic compositions comprising at least one fatty phase, and further has the additional advantages of having a <<neutral>> color which makes it easily assimilable in a cosmetic composition, and of containing only little or no organic solvent.

The extract obtained by the extraction method described earlier is particularly suitable for incorporation into fatty phases of cosmetic compositions intended for care or making up the skin, the lips or integuments.

A fourth object of the present invention thus deals with a cosmetic composition comprising a lipophilic extract as defined earlier.

Said extract may advantageously be contained in the fatty phase of oil-in-water emulsions such as skin care creams, or in fatty phases of compositions such as lipsticks or mascaras.

Moreover, said cosmetic composition also comprises one or more cosmetically acceptable active agents.

Said cosmetic composition may also comprise, as active agents, molecules or extracts selected from: substances having skin-lightening activity; substances having slimming activity; substances having moisturizing activity; substances having calming, soothing or relaxing activity; substances having an activity which stimulates skin micro-circulation in order to improve the radiance of the skin tone, in particular of the face, substances having sebo-regulatory activity for the care of fatty skin; substances intended for cleaning or purifying the skin; substances having anti-radical activity; substances intended for softening or delaying the effects of ageing on the skin, in particular formation of wrinkles, by an activity aimed at promoting preservation of the skin structure and/or limiting degradation of the extra-cellular matrix of the surface layers of the dermis and epidermis and/or obtaining a protective, corrective or restructuring effect on the skin; substances having anti-inflammatory activity.

In addition to the at least one active agent and the lipophilic extract of the invention, said cosmetic composition may comprise one or more other cosmetically acceptable excipients, which are applied during the preparation of said composition.

The present invention will be better understood by means of the figures and of their caption and of the additional description which follows, which refers to non-limiting examples of preparation of extracts according to the invention.

EXAMPLES

Example 1

Extraction Methods from Lignified Vine (*Vinis vitifera*) Portions

1) Extraction from Vine Shoots with Carbon Dioxide.

A harvest of vine shoots of the Sauvignon variety is used here.

In order to establish optimum conditions for extraction with carbon dioxide on these shoots, different extraction conditions (pressure, temperature, presence or absence of co-solvent, nature of the co-solvent) are tested, in which the carbon dioxide is in the supercritical or subcritical state. The final color of the obtained extract is recorded, marked out from 1 (very clear) to 4 (very dark) according to an internally established scale and the mass yield of the extraction is calculated.

The different extraction conditions carried out and the obtained results are summarized in Table I hereafter.

TABLE I

| No. | Pressure (MPa) | Temperature | Co-solvent (% w/w) | Mass yield (%) | Color | Color scale |
|---|---|---|---|---|---|---|
| 1 | 29 | 60° C. | — | 0.3-0.6 | Yellow-green | 2 |
| 2 | 29 | 20° C. | — | 0.5-1.4 | Yellow and green sheen | 1 |
| 3 | 29 | 60° C. | ethanol 3% | 0.7 | Dark green black | 4 |
| 4 | 29 | 60° C. | ethanol 1% | 0.8 | green | 3 |
| 5 | 29 | 60° C. | ethanol 6% | 0.9 | Dark green black | 4 |
| 6 | 29 | 60° C. | water 0.3% | 0.3 | Yellow green | 2 |

The results show that at 60° C., with the absence of co-solvent or the use of water, it is possible to obtain a satisfactory (not very colored) lipophilic extract containing little chlorophyll, but with a low extraction mass yield. At the same temperature, the use of ethanol leads to the presence of chlorophyll which strongly colors the final extract, which is discarded.

With extraction under subcritical conditions (T=20° C.), at a high pressure ($29.10^6$ Pa), it is possible to obtain an extract with a low amount of chlorophyll, with satisfactory extraction yield. This lipophilic extract may be directly used in cosmetics without any prior <<discoloration>>.

2) Lipophilic Extract of Vine Shoots with Carbon Dioxide in the Subcritical State.

Taking into account the results obtained in the preceding paragraph, 450 grams of dried and beforehand milled vine shoots are treated under defined conditions (20° C., $29.10^6$ Pa, without any co-solvent). Finally, 6.5 grams of lipophilic extract (mass yield of 1.4% w/w) are obtained with residual water. This very clear colored extract, because it is not very loaded with chlorophyll, appears as a solid at room temperature. The extract is then dried by freeze-drying.

With the extraction conditions used here, it is possible to obtain a lipophilic extract rich in nutritive components of the skin.

An investigation with High Pressure Liquid Chromatography (HPLC) confirms that with the specifically selected extraction procedure, it is possible to obtain an extract with low chlorophyll content.

3) Lipophilic Extract from Vine Shoots with Carbon Dioxide in the Subcritical State in the Presence of a Stripping Agent.

Taking into account the results obtained in the preceding paragraph, 450 grams of dried and beforehand milled vine shoots are treated under conditions as defined previously (20° C., $29.10^6$ Pa, without any co-solvent) and in the presence of an excipient, dicaprylyl carbonate, which plays the role of a stripping agent. Dicaprylyl carbonate at the end of purification accounts for nearly 95% of the obtained wax, the yield being thereby standardized to 50% relatively to the mass of plant material and of dicaprylyl carbonate introduced into the extractor.

Finally, 0.05% by mass of dl-α-tocopherol are added to the obtained extract as an antioxidant.

The detail of the analysis of the obtained extract is detailed in Tables IIa and IIb hereafter.

TABLE IIa

| Compounds | Mass yield (%) |
|---|---|
| Free fatty acids | 30.9 |
| Monoglycerides | 4.4 |
| Diglycerides | 9.6 |
| Triglycerides | 10.3 |
| Sterol + alcohol | 30.7 |
| Sterol ester | 2.5 |
| Hydrocarbon | 1.2 |
| Waxes | 3.5 |
| Unidentified | 0.6 |

TABLE IIb

| Compounds | Mass yield (%) |
|---|---|
| Aliphatic alcohols | 11.9 |
| Terpenic alcohols | 9.6 |

The analysis of the obtained extract finally revealed that the latter contained fatty acids (oleic acid, linoleic acid, palmitic acid, linolenic acid, stearic acid, behenic acid) and sterols (β-sitosterol, stigmasterol, campesterol, stigmastanol). On the other hand, the same analysis demonstrated that this extract did not contain any resveratrol, sugars, amino acids, saponins, or tannins.

4) Extraction from Vine Roots with Carbon Dioxide.

For this test, a harvest of vine roots of the Sauvignon variety is used. In order to establish the efficiency of an extraction with carbon dioxide on these roots, different extraction conditions are tested (20° C. or 60° C., $18.10^6$ Pa or $29.10^6$ Pa, either presence of a co-solvent or not) in which the carbon dioxide is in the supercritical state. The final color of the extract is recorded, marked out as 1 (very clear) to 4 (very dark) according to an internally established scale and the extraction mass yield is calculated.

The different extraction conditions tested and the obtained results are summarized in Table III hereafter.

TABLE III

| No. | Pressure (Mpa) | Temperature | Co-solvent (% w/w) | Mass yield (%) | Color | Scale |
|---|---|---|---|---|---|---|
| 1 | 18 | 60° C. | — | 0.05 | yellow | 1 |
| 2 | 29 | 60° C. | — | 0.1 | yellow | 1 |
| 3 | 29 | 60° C. | ethanol 3% | 1.1 | yellow | 1 |

The results show that, by using ethanol as a co-solvent, the achieved extraction mass yield is higher than with the method excluding it.

5) Lipophilic Extract from Vine Roots with Carbon Dioxide in the Supercritical State Considering the results obtained under 3), 450 grams of dried roots of the Sauvignon variety are treated and milled beforehand, under defined conditions (60° C., $29.10^6$ Pa, with 3% ethanol relatively to the carbon dioxide). Finally 4.9 grams of extract are obtained (mass yield of 1.1%) only containing residual traces of co-solvent. The extract appears as a solid at room temperature.

With these extraction conditions it is possible to obtain an extract rich in fats, which may be used as an excipient in cosmetic compositions.

Example 2

Cosmetic Composition Comprising the Lipophilic Extract According to the Invention The extract from vine shoots, prepared according to paragraph 2 of Example 1, is incorporated into the fatty phase of an oil-in-water cosmetic emulsion, the formula of which is detailed below (% expressed by weight of the composition):

| | |
|---|---|
| Vine shoot extract | 1 |
| Anti-wrinkle plant extract | 0.1 |
| Surfactant (Arlacel ® 165 VP) | 5 |
| Cetyl alcohol 95% | 1 |
| Stearyl alcohol | 1 |
| Beeswax | 1.5 |
| Oil (Perleam ®) | 8.5 |
| Tri caprate/caprylate glycerides | 3 |
| Dimethicone 100 CS | 1 |
| Polymer (Keltrol ®) | 0.4 |
| Sodium hydroxide | 0.04 |
| Powdered tetrasodium EDTA | 0.1 |
| Preservatives | 0.5 |
| Perfumes | <0.1 |
| Water | qsp 100 |

The obtained composition is an anti-wrinkle care cream.

Example 3

Cosmetic Composition Comprising the Lipophilic Extract According to the Invention The vine root extract, prepared according to paragraph 4 of Example 1 is incorporated into the formula of a mascara, the detail of which is specified below (% expressed by weight of the composition):

| | |
|---|---|
| Vine root extract | 1 |
| Coloring agent | 20.0 |
| $C_{18-36}$ triglycerides | 9.9 |
| Glyceryl stearate | 12.0 |
| Beeswax | 4.6 |
| Carnauba wax | 2.2 |
| Triethanolamine | 1.9 |
| SHELLAC | 1.9 |
| Stearic acid | 1.9 |
| Palmitic acid | 1.9 |
| Hydrogenated glyceryl rosinate | 1.5 |
| PVP/VA copolymer | 1.0 |
| Lecithin | 1.0 |
| Preservatives | 0.6 |
| Xanthan gum | 0.4 |
| Phenoxyethanol | 0.2 |
| Hydrolyzed keratin | 0.2 |
| Tetrasodium EDTA | <0.1 |
| Perfumes | <0.1 |
| Water | qsp 100 |

The obtained make-up composition is a mascara.

The invention claimed is:

1. A method for preparing a colorless lipophilic extract from lignified portions of *vitis vinifera*, comprising extracting the colorless lipophilic extract from lignified portions of *vitis vinifera* stock, with an apolar solvent comprising carbon dioxide ($CO_2$) in the subcritical state.

2. The method of claim 1, wherein the *vitis vinifera* is from a variety selected from the group consisting of Merlot, Cabernet Franc, Gamay, Syrah, Semillon and Sauvignon varieties.

3. The method of claim 1, wherein the carbon dioxide is compressed at a pressure higher than or equal to $7.4.10^6$ Pa.

4. The method of claim 1, wherein the extraction is carried out at a temperature between 18° C. and 25° C.

5. The method of claim 4, wherein the extraction is carried out at a temperature of 20° C.

6. The method of claim 1, wherein the extraction is carried out in the absence of a co-solvent.

7. The method of claim 6, wherein the extraction is carried out at a temperature below the critical temperature of carbon dioxide.

8. The method of claim 1, wherein the extraction is carried out at a temperature of 20° C. and at a pressure of $29.10^6$ Pa.

9. The method of claim 1, wherein the carbon dioxide is compressed at a pressure higher than or equal to $18.10^6$ Pa.

10. The method of claim 1, wherein the carbon dioxide is compressed at a pressure higher than or equal to $25.10^6$ Pa.

11. The method of claim 1, wherein the lignified portions of *vitis vinifera* stock comprise shoots and the extracting is conducted in the absence of a co-solvent.

12. The method of claim 1, wherein the lignified portions of *vitis vinifera* are dried.

\* \* \* \* \*

UNITED STATES PATENT AND TRADEMARK OFFICE
CERTIFICATE OF CORRECTION

PATENT NO.      : 8,974,842 B2
APPLICATION NO. : 12/460742
DATED           : March 10, 2015
INVENTOR(S)     : Virginie Pecher and Patrice Andre Page 1 of 1

It is certified that error appears in the above-identified patent and that said Letters Patent is hereby corrected as shown below:

In the Claims,

Column 8, line 27, "Semillon" should read --Sèmillon--.

Signed and Sealed this
Eighth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,974,842 B2
APPLICATION NO. : 12/460742
DATED : March 10, 2015
INVENTOR(S) : Virginie Pecher and Patrice Andre Page 1 of 1

It is certified that error appears in the above-identified patent and that said Letters Patent is hereby corrected as shown below:

In the claims,

Column 8, line 24, delete "Semillon" and insert therefor --Sémillon--.

Signed and Sealed this
First Day of March, 2016

Michelle K. Lee
*Director of the United States Patent and Trademark Office*